United States Patent [19]
Ishikawa et al.

[11] Patent Number: 5,908,656
[45] Date of Patent: Jun. 1, 1999

[54] THERMOFORMED MEDICAL DEVICE WITH LUBRICIOUS MODIFIED POLYETHYLENE OXIDE LAYER

[75] Inventors: Kenji Ishikawa; Hideaki Kitou; Kenichi Shimura; Yasunobu Zushi; Naoki Ishii; Taku Aoike, all of Kanagawa, Japan

[73] Assignee: Terumo Kabushiki Kaisha, Tokyo, Japan

[21] Appl. No.: 08/890,965

[22] Filed: Jul. 10, 1997

Related U.S. Application Data

[63] Continuation-in-part of application No. 08/687,056, Aug. 8, 1996, abandoned.

[30] Foreign Application Priority Data

Aug. 9, 1995 [JP] Japan ..................... 7-203370

[51] Int. Cl.$^6$ ................ B05D 3/10; B05D 3/12
[52] U.S. Cl. .................. 427/2.3; 427/2.1; 427/160; 427/333; 427/370; 264/173.19
[58] Field of Search ............... 264/173.19; 427/2.28, 427/2.3, 333, 370, 160, 371, 393.5, 2.1

[56] References Cited

U.S. PATENT DOCUMENTS

| | | |
|---|---|---|
| 4,100,309 | 7/1978 | Micklus et al. . |
| 4,119,094 | 10/1978 | Micklus et al. . |
| 4,373,009 | 2/1983 | Winn . |
| 4,459,317 | 7/1984 | Lambert . |
| 4,487,808 | 12/1984 | Lambert . |
| 4,540,407 | 9/1985 | Dunn ........................ 604/292 |
| 4,722,344 | 2/1988 | Cambron et al. ................. 128/658 |
| 4,898,591 | 2/1990 | Jang et al. ................. 604/282 |
| 5,015,238 | 5/1991 | Solomon et al. ................. 604/164 |
| 5,041,100 | 8/1991 | Rowland et al. ................. 604/265 |
| 5,061,424 | 10/1991 | Karimi et al. ................. 264/173.19 |
| 5,229,211 | 7/1993 | Murayama et al. ................. 428/424.4 |
| 5,295,978 | 3/1994 | Fan et al. ................. 606/129 |
| 5,342,693 | 8/1994 | Winters et al. ................. 428/447 |
| 5,346,892 | 9/1994 | Fitt et al. ................. 604/265 |
| 5,352,515 | 10/1994 | Jarrett et al. ................. 606/231 |
| 5,453,467 | 9/1995 | Bamford et al. ................. 427/2.24 |
| 5,576,072 | 11/1996 | Hostettler et al. . |
| 5,670,558 | 9/1997 | Onishi et al. ................. 523/112 |
| 5,702,754 | 12/1997 | Zhong ................. 427/302 |

FOREIGN PATENT DOCUMENTS

| | | |
|---|---|---|
| 0439908 | 8/1991 | European Pat. Off. . |
| 0454293 | 10/1991 | European Pat. Off. . |
| 0592870 | 4/1994 | European Pat. Off. . |
| WO 8602087 | 4/1986 | WIPO . |
| WO 9107200 | 5/1991 | WIPO . |

OTHER PUBLICATIONS

European Search Report dated Dec. 16, 1996.

*Primary Examiner*—Diana Dudash
*Attorney, Agent, or Firm*—Burns, Doane, Swecker & Mathis, L.L.P.

[57] ABSTRACT

This invention provides a medical device in which its lubricity is continually maintained and its safety is guaranteed.

Particularly, it provides a medical device in which lubricity is generated on at least a portion of its surface when the device is contacted with body fluids or exposed to physiological aqueous conditions, wherein the lubricity-generating portion is formed by thermoforming.

6 Claims, 1 Drawing Sheet

THERMOFORMED MEDICAL DEVICE WITH LUBRICIOUS MODIFIED POLYETHYLENE OXIDE LAYER

This application is a continuation, of application No. 08/687,056, filed Aug. 8, 1996, abandoned.

FIELD OF THE INVENTION

This invention relates to a medical device and a production process thereof. Particularly, it relates to a medical device in which lubricity is generated on its surface when the device is contacted with body fluids or exposed to physiological aqueous conditions and to a production process thereof. More particularly, it relates to a medical device in which lubricity is generated on its surface when the device is contacted with body fluids or exposed to physiological aqueous conditions as a result of its insertion into the living body to carry out a medical treatment or a diagnosis.

BACKGROUND OF THE INVENTION

Tissue injuries such as mucosal injury, vascular injury and the like occur when general medical devices composed of plastics, metals, ceramics and the like are inserted into the living body and contacted strongly with biological tissues. In concrete terms, when a catheter, a guide wire, an endoscope, a rectal thermometer probe or the like is inserted into a blood vessel, a digestive organ or the like hollow organ until it reaches the intended position, various tissue injuries including mucosal injury and vascular injury occur which give patients pain and cause prolongation of therapeutic period. Also, in some cases, a medical device cannot be inserted into the intended position due to its large insertion resistance. In consequence, in order to lessen these injuries or reduce the insertion resistance, various measures have been taken in the prior art for example by using a low friction material as the base material, coating the device surface with oils which give lubricity or with a hydrophilic polymer or fixing a hydrophilic polymer to the surface making use of covalent bond, ionic bond and the like chemical bonds.

Illustrative examples of the low friction material include polyethylene, polyacetal, fluorocarbon resin and the like, and those of the lubricity-providing oil include silicone oil, olive oil, glycerol and the like. With regard to the method for fixing a hydrophilic polymer to the material surface, JP-B-59-19582 discloses a method in which polyvinyl pyrrolidone or the like is fixed making use of isocyanate group (the term "JP-B" as used herein means an "examined Japanese patent publication"), JP-A-59-81341 discloses a method in which two or more hydrophilic polymers are fixed also making use of isocyanate group (the term "JP-A" as used herein means an "unexamined published Japanese patent application") and JP-A-58-193766 discloses a method in which polyethylene oxide is fixed also making use of isocyanate group. However, such low friction materials are not effective in sufficiently preventing tissue injuries, and continual presence of lubricity cannot be obtained by the method in which oils or hydrophilic polymers are used. Also, since a substance having high reactivity (isocyanate group or the like) is used in the fixation of a hydrophilic polymer to the surface, it is probable that the substance when remained will cause a problem due to its toxicity. In addition, when the method in which an oil or a hydrophilic polymer is used is employed in the production process of medical devices, the process becomes complex due, for example, to the increased number of operation steps.

Thus, as has been described in the foregoing, the prior art methods for adding lubricity to the surface of a medical device have disadvantages in that production process of the device becomes complex, its lubricity cannot be maintained continually and when chemicals having high reactivity are used, its safety cannot be maintained depending on a situation.

SUMMARY OF THE INVENTION

In view of the above, it therefore becomes an object of the present invention to provide a medical device in which its effects are continually maintained and its safety is guaranteed by employing a method which is simpler than the conventional coating method.

(1) Particularly, in accordance with the present invention, there is provided a medical device in which lubricity is generated on at least a portion of its surface when the device is contacted with body fluids or exposed to physiological aqueous conditions, wherein the improvement resides in that the lubricity-generating portion is formed by thermoforming.

(2) Preferably, at least a portion of the lubricity-generating portion arranged on at least a portion of the surface of the device is comprised of cross-linked polyalkylene oxide, a derivative of polyalkylene oxide or a compound (or a polymer) having a derivative of polyalkylene oxide.

(3) Another embodiment, there is provided the medical device wherein a chemical reaction takes place between a surface layer having the lubricity generating portion and a layer under thereof constituting the device while the device is formed under heating.

(4) Preferably, the polyalkylene oxide comprises a recurring unit having a ratio of carbon to oxygen atom (C/O) is up to 3.

Other objects and advantages of the present invention will be made apparent as the description progresses.

DETAILED DESCRIPTION OF THE INVENTION

Figure 1:
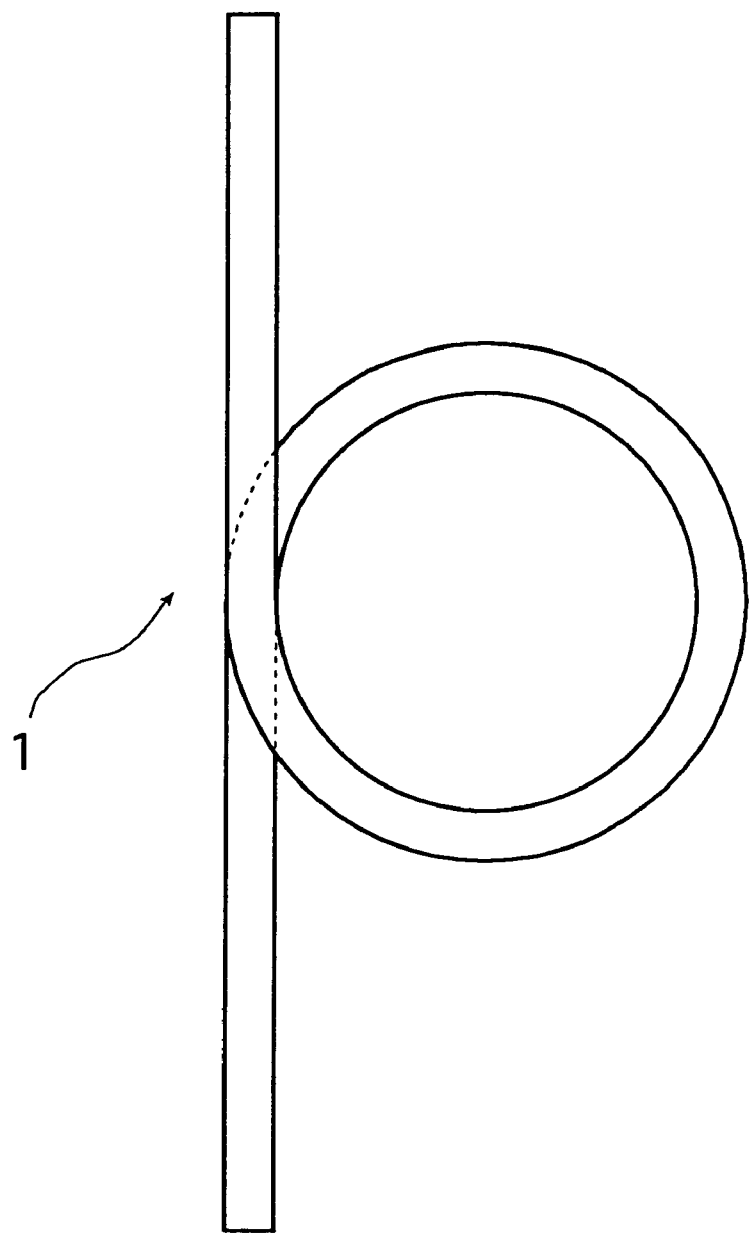
FIG. 1 is a schematic illustration of a simulated blood vessel for use in the evaluation of lubricity of the medical device of the present invention, in which the character 1 represents the simulated blood vessel.

Unlike the prior art materials prepared by coating or making use of a chemical bond-aided polymer reaction, the material to be used in at least a portion of the lubricity-generating portion of the present invention is a material capable of undergoing thermoforming. That is, it has a thermoplastic property. The material is not particularly limited with the proviso that it is a thermoplastic resin which generates lubricity by incorporating water and the like when it is contacted with body fluids or exposed to physiological aqueous conditions. In any case, a hydrophilic thermoplastic resin, particularly polyalkylene oxide, such as polyethylene oxide or polypropylene oxide, may be used suitable as the material. Preferably, polyalkylene oxide comprises a recurring unit having a number ratio of carbon to oxygen atom (C/O) up to 3. For example, ethylene oxide, [C/O ratio og 2], propylene oxide [C/O ratio of 3]or dioxolane [C/O ratio of 1.5]may be listed. However, since such a material shows insufficient strength under its dry or wet state in some cases depending on its use, it is more desirable to form partial cross-linking in order to improve the strength without spoiling its function. Though not particularly limited, the cross-linking may be effected by the use of a peroxide. The preferred cross-linking ratio based on volume swell(%) is at least 300% under the conditions of its use, such as in an physioligical saline or body fluid. The preferable molecular weight of polyalkylene oxide used in the present invention is 5,000 to 5,000,000, more preferably 20,000 to 1,000,000, especially 100,000 to 500,000 is preferred for polyethylene oxide.

In addition, the material to be used in at least a portion of the lubricity-generating portion of the present invention may be a derivative of polyalkylene oxide such as polyethylene oxide or a compound (polymer) having a derivative of polyalkylene oxide.

For example, a derivative of polyalkylene oxide may be a polyalkylene oxide modified at one end or both ends with such groups as amino, carboxyl, thiol, epoxy and aldehyde.

For example, such urethane or polyamide compounds having a polyethylene oxide derivative modified at one end or both ends with such groups as amino, carboxyl, thiol, epoxy and aldehyde are expected to fortify the adhesive force on the surface of the medical device by the modified functional group in addition to the lubricating properties based on the polyalkylene main chain.

Furthermore, when a substance expected to generate lubricity on the surface is composed of a material modified with such compounds having proton-reactive functional groups as maleic anhydride and glycydil(meth)acrylate, and when the substance generating lubricity on the surface is a modified polyethylene oxide having such proton-donating groups as amino, carboxyl and thiol, a chemical bonding is induced on the boundary during forming of the device under heating to result in strong adhesion providing a safer medical device.

The material to be used in at least a portion of the lubricity-generating portion of the present invention is not necessarily a single material, and can be used by mixing it with other materials, particularly other resins. For example, a cross-linked or a derivative of polyalkylene oxide may be used suitably by mixing it with olefinic resins such as polyethylene, polypropylene, modified polyolefin and the like, as well as polystyrene, polyvinyl chloride, polycarbonate, acrylonitrile-butadiene-styrene copolymer, ethylene-vinyl acetate copolymer, polyamide, polyethylene terephthalate and the like. Their mixing ratios are not particularly limited.

Preferably the content of the lubricity generating materials (polymers) is 5 to 95 wt %, more preferably 20 to 80 wt %.

The material to be used in at least a portion of the lubricity-generating portion of the present invention may be used suitably by mixing it with a radiopaque agent such as powder of tungsten, barium sulfate, bismuth oxycarbonate, sodium iodide and the like. Their mixing ratio are not particularly limited, but preferably, the content of the radio opaque agent is up to 50 wt %, more preferably 20 to 45 wt %. In this embodiment, the medical device of the present invention has radio opaque properties as well as lubricating properties.

Though the thermoforming of the present invention is not particularly limited, it may be effected preferably by extrusion molding, multilayer extrusion molding, profile extrusion molding, injection molding, multiple color injection molding, insert injection molding, press molding, vacuum press molding and the like means. Each of these thermoforming means is conventional molding method and does not require a special making machine or special molding techniques. That is, forming of a crystalline resin may be carried out at a temperature which is higher than its melting point by a factor of approximately 10 to 40° C., and an amorphous resin may be formed at a temperature which is higher than its glass transition point by a factor of approximately 80 to 150° C. A hollow shape product such as a catheter or the like may be formed by extrusion molding, or by co-extrusion molding together with a base material resin which forms inner layer when it is desirable to obtain lubricity only on the outermost surface of a catheter. The thermoforming can also be applied to a member which is formed by injection molding, such as a rectal thermometer probe. In order to add lubricity only to the outermost surface of said probe, two color (multiple color) injection molding or insert injection molding may be effective. Also, when a thin dish-like product is formed, press molding or vacuum press molding may be used. In addition, a press-molded product having lubricity only on its outermost surface can be obtained making use of a multi-layer sheet having a lubricity material on its surface prepared in advance by co-extrusion molding. Alternatively, two or more members molded in advance by thermoforming may be made into a composite structure making use of an adhesive resin, adhesive agent or the like. In comparison with the conventional materials obtained by a coating method or a chemical bond-aided polymer reaction, the lubricity-generating portion can be formed more thickly by each of these molding methods, so that its peeling does not occur during operation of a medical device and continual presence of its function can be expected.

The medical device of the present invention is a device which is used by contacting it with body fluids such as blood, lymph, saliva, tears, gastric juice, urine and the like or with physiological aqueous systems such as physiological saline, ion concentration-adjusted buffer solutions and the like. Since its contact with these liquids generates lubricity on its surface, workability of said medical device, such as easy insertion into the aimed position, is improved and tissue injuries can be reduced. Though not particularly limited, the medical device of the present invention is used for medical treatment or diagnosis in the aforementioned manner, preferably as a catheter, a guide wire, an endoscope, a rectal thermometer probe and the like.

EXAMPLES

The following examples are provided to further illustrate the present invention. It is to be expressly understood, however, that the medical devices, materials and molding methods described in the examples are for purpose of illustration only and are not intended as a definition of the limits of the invention.

Inventive Example 1

A catheter in the form of a multi-layer tube of 4.0 mm in outer diameter and 2.0 mm in inner diameter was obtained by co-extruding a cross-linked polyethylene oxide (AQUACALK®, manufactured by Sumitomo Fine Chemical) as the outer layer and a maleic anhydride-modified polyethylene (MODIC®, manufactured by Mitsubishi Petrochemical) as the inner layer from a two-layer die at a die temperature of 105° C. When the tube was cut at a right angle to the major axis and its two-layer structure was observed using a projector, each layer was found to have a thickness of about 0.5 mm and the interface was sufficiently adhered. A simulated blood vessel 1 of 6 mm in inner diameter which has been prepared from polyvinyl chloride and filled with physiological saline was made into a loop-like shape of 50 mm in radius (see FIG. 1), and the catheter tube obtained above was inserted into the thus prepared blood vessel (insertion length, 500 mm; insertion rate, 50 mm/min; 37° C.) to measure the value of resistance with a tensile tester. The results are shown in Table 1. When insertion and ejection of the tube were repeated 100 times, peeling was not observed and its lubricity was maintained. Also, an eluting material test by a "disposable arteriovenous indwelling catheter" (Manual on Standards and Criteria of Medical Tools, pp. 271–273, 1991, published by Yakugyo Jiho-sha) was carried out, with the results also shown in Table 1.

Inventive Example 2

Using a 50:50 (weight ratio) mixture of a cross-linked polyethylene oxide (AQUACALK®, manufactured by Sumitomo Fine Chemical) and a polyamide elastomer (Ube Nylon PAE, manufactured by Ube Industries) prepared by a twin screw extruder, a catheter in the form of a single-layer tube of 4.0 mm in outer diameter and 2.0 mm in inner diameter was obtained. The value of resistance at the time of its insertion was measured in the same manner as described in Inventive Example 1, with the results shown in Table 1. When insertion and ejection of the tube were repeated 100 times, peeling was not observed and its lubricity was maintained. Results of its eluting material test are also shown in Table 1.

Inventive Example 3

Using a 25:75 (weight ratio) mixture of a cross-linked polyethylene oxide (AQUACALK®, manufactured by Sumitomo Fine Chemical) and an acrylonitrile-butadiene-styrene copolymer (ABS, manufactured by Japan Synthetic Rubber) prepared by a twin screw extruder, a rectal thermometer probe (a taper-like shape having a minimum diameter of 8 mm, a maximum diameter of 12 mm and a length of 100 mm) was obtained by injection molding. Using a vulcanized natural rubber tube of 10 mm in inner diameter and 50 mm in length as a simulated anus, the thus obtained probe wetted with physiological saline was inserted into the simulated anus (insertion length, 45 mm; insertion rate, 100 mm/min; 37° C.) to measure the value of resistance with a tensile tester. The results are shown in Table 2. When insertion and ejection of the probe were repeated 100 times by wetting it with physiological saline prior to each insertion, peeling was not observed and its lubricity was maintained. Results of its eluting material test are also shown in Table 2.

Comparative Example 1

A catheter was formed in the same manner as described in Inventive Example 1, except that the maleic anhydride-modified polyethylene (MODIC®, manufactured by Mitsubishi Petrochemical) was used alone. The value of resistance at the time of its insertion into a simulated blood vessel was measured in the same manner as described in Inventive Example 1, with the results shown in Table 1.

Comparative Example 2

A catheter was obtained in the same manner as described in Inventive Example 2, except that the cross-linked polyethylene oxide (AQUACALKE®, manufactured by Sumitomo Fine Chemical) was not used. The value of resistance at the time of its insertion into a simulated blood vessel was measured in the same manner as described in Inventive Example 1, with the results shown in Table 1.

Comparative Example 3

A probe was obtained in the same manner as described in Inventive Example 3, except that the cross-linked polyethylene oxide (AQUACALK®, manufactured by Sumitomo Fine Chemical) was not used. The value of resistance at the time of its insertion into a simulated anus was measured in the same manner as described in Inventive Example 3, with the results shown in Table 2.

Inventive Example 4

A mixture of a modified polyethylene oxide (PAOGEN®, manufactured by Daiichi Kogyo Seiyaku) and 45 wt % of a fine tungsten powder (particle size ca.3–4 $\mu$m) as radiopaque agent were melted and kneaded to obtain a raw material containing a radiopaque agent. PAOGEN: polyethylene oxide of molecular weight about 10000 is modified with polycarboxylic acid for chain extention to molecular weight of about 100000.

A three layered tube was prepared by use of the raw material as the outer layer, a maleic anhydride-modified polyethylene (BONDINE® HX8290, manufactured by Sumitomo Chemical) as the middle layer (adhesive layer) and a urethane (MIRACTRAN® P395, manufactured by Nippon Miractoran) as the inner layer. A catheter wire for shadow-forming of blood vessel was prepared by covering with the three-layered tube an inner core of a 51%Ni—Ti alloy having the length of 1800 mm, tip opening of 0.06 mm diameter, bottom opening of 0.25 mm diameter and a 120 mm tapered portion down to the tip opening. Thus obtained wire had the total length of 1800 mm and diameter of around 0.8 mm.

TABLE 1

|  | Material name | Molding method | Value of resistance (gf) | Eluting material test |
|---|---|---|---|---|
| Inventive Example 1 | polyethylene oxide/ maleic anhydride-modified polyethylene | co-extrusion molding | 28 | adaptable |
| Inventive Example 2 | polyethylene oxide/ polyamide elastomer | extrusion molding | 40 | adaptable |
| Comparative Example 1 | maleic anhydride-modified polyethylene | extrusion molding | 160 | — |
| Comparative | polyamide elastomer | extrusion | 240 | — |

TABLE 1-continued

|  | Material name | Molding method | Value of resistance (gf) | Eluting material test |
|---|---|---|---|---|
| Example 2 |  | molding |  |  |
| Inventive Example 4 | modified polyethylene oxide/maleic anhydride-modified polyethylene/urethane | extrusion molding | 24 | adaptable |
| Comparative Example 4 | maleic anhydride-modified polyethylene/urethane | extrusion molding | 185 | — |

TABLE 2

|  | Material name | Molding method | Value of resistance (gf) | Eluting material test |
|---|---|---|---|---|
| Inventive Example 3 | polyethylene oxide/ABS copolymer* | extrusion molding | 16 | adaptable |
| Comparative Example 3 | ABS copolymer* | extrusion molding | 370 |  |

*ABS copolymer: acrylonitrile-butadiene-styrene copolymer

Using a polyvinyl chloride tube of 1 mm inner diameter as the simulated blood vessel 1 of FIG. 1, experiments similar to those of Inventive Example 1 were repeated. The result is shown in Table 1.

The 100 times insertion and ejection of the wire showed no remarkable increase in the peeling and resistance, and the lubricity was maintained. Further, the eluting material test was conducted in a similar manner as that of Inventive Example 1, and the result was adaptable (see Table 1).

Comparative Example 4

Without using the modified polyethylene oxide of Inventive Example 4 (PAOGENE®, manufactured by Daiichi Kogyo Seiyaku), the tungsten fine powder and a maleic anhydridemodified polyethylene (BONDINE® HX8290, manufactured by Sumitomo Chemical) were melted and kneaded to obtain a raw material containing a radiopaque agent.

By use of the raw material for the outer layer, a catheter for radiopaque of blood vessel was prepared Resistance to the insertion and ejection of the wire were measured similarly, and the result is shown in Table 1.

Inventive Example 5

By a multi-layered blow molding method, were obtained gloves for touch of anus having a styrene elastomer (RABALON® ME6301, manufactured by Mitsubishi Petrochemical) as the inner layer, a maleic anhydride-modified polyethylene (MODIC® E-20OH, manufactured by Mitsubishi Petrochemical) as the middle layer and a terminally aminated polyethylene oxide (PEO amine # 6000, manufactured by Kawaken Finechemical) as the inner layer.

Though the glove showed no lubricity on the dry surface, however, the surface lubricity generated so well when wetted with physiological saline as such lubricating agents as jelly and oils were unnecessary.

Comparative Example 5

Gloves for touch of anus were obtained by the similar method to that of Inventive Example 5 with the exception that no terminally aminated PEO (PEO amine # 6000, manufactured by Kawaken Finechemical) was used.

The glove showed no lubricity on the surface in dry or wet conditions, and such lubricating agents as jelly and oils were necessary for using the glove.

As is evident from the above tables, all moldings of the inventive examples have smaller values of resistance than those of the comparative examples, showing generation of lubricity in the inventive products.

Thus, it is apparent that there has been provided, in accordance with the present invention, a medical device in which lubricity is generated on at least a portion of its surface when the device is contacted with body fluids or exposed to physiological aqueous conditions. Since the inventive medical device is characterized in that said lubricity-generating portion is formed by thermoforming, lubricity can be added to the surface of the device markedly easily in comparison with the conventional method in which an oil is applied or a lubricity material is coated. In addition, its function is continually maintained, its peeling and the like do not occur and it meets the required eluting material test which means its excellent safety.

What is claimed is:

1. A process for producing a medical device comprising a substrate and lubricity-expressing surface layer disposed on at least a portion said substrate, wherein said lubricity-expressing surface layer becomes lubricant when it is brought in contact with a body fluid or under physiological aqueous conditions, said process comprising the step of:
    (a) thermoforming the lubricity-expressing surface layer and the substrate, wherein,
        (i) said lubricity-expressing surface layer comprises a modified polyethylene oxide containing at least one reacting group selected from the group consisting of amino group, carboxyl group, and thiol group; and
        (ii) said substrate comprises a polymer modified with at least one member selected from the group consisting of maleic anhydride, glycidyl (meth)acrylate, and derivatives thereof, and wherein said process is effected (b) under conditions whereby said reacting group of the polyethylene oxide of the lubricity-expressing surface layer reacts with said reacting group of the polymer of the substrate during thermoformation.

2. The process according to claim 1, wherein said modified polyethylene oxide of the lubricity-expressing surface layer has a molecular weight ranging from 5,000 to 500,000.

3. The process according to claim 1, wherein said lubricity-expressing surface layer comprises a cross-linked modified polyethylene oxide.

4. The process according to claim 1, wherein said lubricity-expressing surface layer further comprises a radiopaque agent.

5. The process according to claim 4, wherein said agent is selected from the group consisting of tungusten, barium, sulfate, bismuth oxycarbonate, and sodium iodide.

6. The process of claim 1, wherein the medical device comprises a catheter.

* * * * *